United States Patent [19]
Koike et al.

[11] Patent Number: 4,949,365
[45] Date of Patent: Aug. 14, 1990

[54] APPARATUS FOR MEASURING DENSITY OR THE LIKE OF AN OBJECT HAVING A SMALL TRANSMISSION FACTOR

[75] Inventors: Kiyoshi Koike; Hiroshi Uchida; Keisuke Masuda; Tatsuro Hayashi, all of Shizuoka; Rikushi Morita, Kyoto, all of Japan

[73] Assignee: Hamamatsu Photonics Kabushiki Kaisha, Hamamatsu, Japan

[21] Appl. No.: 312,343

[22] Filed: Feb. 16, 1989

Related U.S. Application Data

[63] Continuation of Ser. No. 928,404, Nov. 10, 1986, abandoned.

[30] Foreign Application Priority Data

Nov. 8, 1985 [JP] Japan .................. 60-250315

[51] Int. Cl.$^5$ ............................................. G01B 15/02
[52] U.S. Cl. ........................................ 378/54; 250/369
[58] Field of Search .................... 378/53, 54, 55, 56; 250/369

[56] References Cited

U.S. PATENT DOCUMENTS

| | | | |
|---|---|---|---|
| 3,373,286 | 9/1964 | Han | 378/147 |
| 3,997,794 | 12/1976 | York et al. | 250/363.10 |
| 4,136,283 | 1/1979 | Blum | 378/149 |
| 4,197,460 | 4/1980 | Anger | 250/363.10 |
| 4,455,616 | 6/1984 | Inbar | 250/369 |
| 4,672,542 | 6/1987 | Roux et al. | 250/369 |

OTHER PUBLICATIONS

Le Blanc et al., "High Resolution Bone Mineral Densotometry with a Gamma Camera", Phys. Med. Biol., 1984, vol. 29, No. 1, 25-30.
Tomomitsu et al., "Dual Photon Absorptiometry", 5/23/86.

*Primary Examiner*—Craig E. Church
*Attorney, Agent, or Firm*—Finnegan, Henderson, Farabow, Garrett and Dunner

[57] ABSTRACT

An apparatus for measuring the density or the like of an object from the level of transmission through the object of gamma rays having different energy levels which are transmitted at the object by a gamma source having a predetermined solid angle of transmission. A collimator collimates gamma transmitted through the object and a scintillator generates light corresponding to the output of the collimator. Plural photomultipliers generate position-dependent electrical signals corresponding to the light generated by an incident gamma ray photon to the scintillator. A calculating circuit generates a density spectrum for the object from the position-dependent electrical signals by integrating the position-dependent electrical signals corresponding to each of the incident gamma ray photons to the scintillator.

10 Claims, 5 Drawing Sheets

APPARATUS FOR MEASURING DENSITY OR THE LIKE OF AN OBJECT HAVING A SMALL TRANSMISSION FACTOR

This application is a continuation, of application Ser. No. 06/928,404, filed Nov. 10, 1986.

FIELD OF THE INVENTION

The present invention relates to an apparatus for measuring density or the like of an object having a small transmission factor, which is suitable for measuring density or a similar property of an object, such as a bone of a human body, which transmits a low level of gamma rays therethrough when compared with surrounding tissues of the human body.

BACKGROUND OF THE INVENTION

An apparatus has been known in which the quantity of bone mineral of a living body can be measured by measuring the degree of transmission of a low-energy gamma ray beam. Such apparatus is described in "A Bone Density Measuring Apparatus," the Medical Radiation Apparatus Technical Handbook, published by the Japan Industries Association of Radiation Apparatus, Apr. 1, 1983. This bone density measuring apparatus uses a shielded ray source for emitting gamma rays in the form of a beam. The ray source and a scintillation detector are separated from each other by an interval of about 15 cm. A portion to be measured is interposed between the ray source and the scintillation detector and the portion to be measured is moved (or scanned) perpendicularly to the gamma rays.

Analog calculations are performed on the basis of the counted number of the gamma rays transmitted through the portion to be measured at every measuring position so as to obtain a value of weight per unit length of the bone in the portion to be measured. There are two methods for measuring the density of a bone or the like: One is a so-called "underwater single ray-source method" in which a portion to be measured is covered with a water bag to make the thickness of material other than the bone a predetermined value and measurement is made by using a single ray-source. The other method is the "aerial two ray-source method" in which a portion to be measured is put in the air and measured by using two ray-sources. The apparatus previously available on the market is arranged so that measurement can be made by either one of the methods. The bone density measuring apparatus includes a scanning device incorporated with a low-energy gamma ray beam generating portion ($^{125}$I 50 mCi and $^{241}$Am 45 mCi being generally used), a special scintillation detector, and a counting device, etc. The final value obtained by the apparatus is a numerical value in proportion to the weight per unit length of the bone.

In carrying out measurement of bone density of a subject by using the above-mentioned apparatus, it is standard to measure bone density along a straight line of a body of the subject, and, therefore, the irradiation with gamma rays must be repeated many times when bone density of a certain portion is to be measured. Accordingly, it has taken several tens of minutes to measure, for example, one of the vertebrae of a man.

OBJECTS AND SUMMARY OF THE INVENTION

An object of the present invention is an apparatus for measuring density or the like of an object having a small transmission factor.

Another object of the present invention is an apparatus for measuring density or the like of an object, such as a bone of a human body, which transmits a low level of gamma rays therethrough when compared with surrounding tissues of the human body.

Still another object of the present invention is an apparatus for measuring the density of an object, such as a bone, in a short time.

These and other objects are achieved by an apparatus for measuring the density or the like of an object having a small gamma ray transmission factor comprising a gamma ray source for emitting gamma rays within a predetermined solid angle from a fixed point; a collimator disposed within a predetermined spatial distance along an axial line from the gamma ray source corresponding to the solid angle and provided with a number of capillaries directed to the fixed point; a scintillator disposed close to the collimator; photomultipliers having photocathodes disposed close to each other and facing the scintillator; and a calculating circuit for specifying incident positions of gamma ray photons to the scintillator or emitting positions of a scintillation light impinging onto the photomultipliers and for integrating an incident frequency at every incident position when the object to be measured is disposed between the gamma ray source and the collimator and is irradiated with gamma rays for a predetermined time.

BRIEF DESCRIPTION OF THE DRAWINGS

The manner by which the above objects and other objects, features, and advantages of the present invention are achieved will become fully apparent from the following detailed description when it is considered in view of the drawings, wherein.

DETAILED DESCRIPTION OF THE INVENTION

Figure 1:
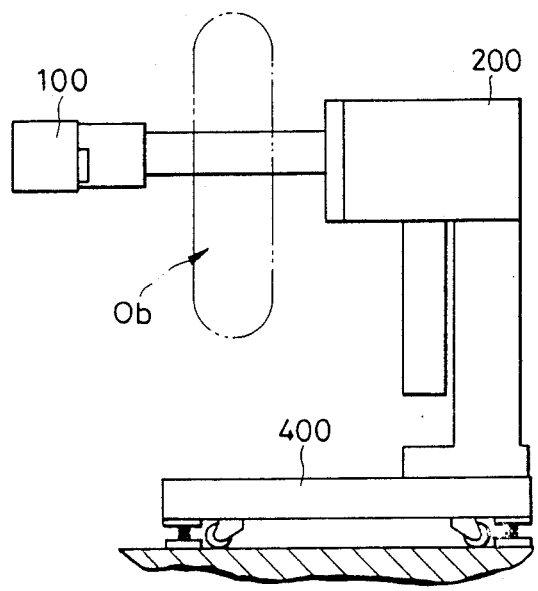
FIG. 1 is a schematic diagram of the density measuring apparatus of the present invention.

FIG. 1 is a diagram of an embodiment of the density measuring apparatus for measuring the density or the like of objects such as vertebrae, according to the present invention. A casing 200 is provided on a caster unit 400. A collimator, a scintillator disposed close to the collimator, and photomultipliers disposed close to each other and having photocathodes facing the scintillator are housed in the casing 200. A casing 100 housing a gamma ray source is disposed in front of the casing 200, and an object to be measured, Ob, is disposed between the casings 100 and 200.

Figure 2:
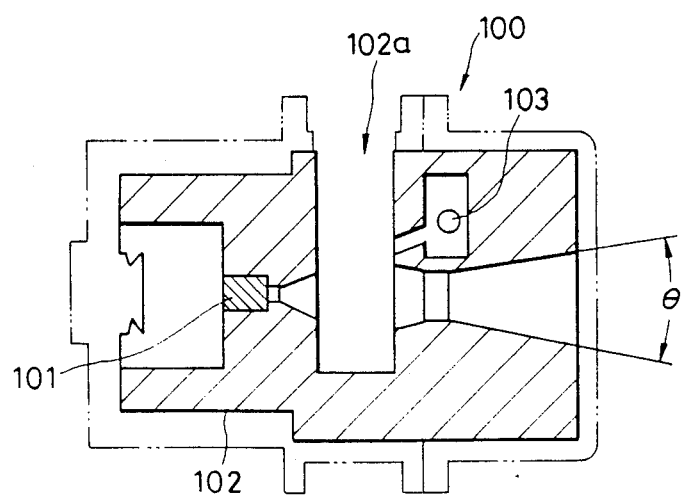
FIG. 2 is a cross-section of a gamma ray source and container of the apparatus of FIG. 1.

FIG. 2 is a cross-section showing the arrangement of the gamma ray source housed in the casing 100. A gamma ray source 101 housed in the casing 100 uses a radioactive material, e.g., $^{153}$Gd. The ray source 101 is accommodated in a lead container 102 and emits gamma rays comprising gamma ray photons over a solid angle $\theta$ of, for example, 16 degrees with respect to an axis of a circular cone in front of the ray source 101. The gamma rays include two types of energy, i.e., 44 kev and 100 kev, with the ratio of quantity of the rays of the two kinds of energy preferably being three to one and the quantity of the rays being 100 mci (millicurie).

Because of the large energy, the gamma rays of 100 kev will be transmitted to a certain extent through a bone. The gamma rays of 44 kev, however, show an extremely low tansmission factor through bone compared with gamma rays of 100 kev. The gamma rays of 44 kev are almost totally absorbed by the bone. The gamma rays of 44 kev, however, show a suitable transmission factor with respect to so-called soft-tissues, such as tissues containing water or fat. It is possible to distinguish the portion of the gamma rays transmitted through the bone from the other portion of the gamma rays transmitted through the soft-tissues by using the above-mentioned two kinds of gamma rays and by analyzing the transmitted gamma rays.

A portion 102a formed in the container 102 is an insertion hole for a shutter. When measurement is not being carried out, a thick lead plate is inserted into this portion to prevent gamma rays from being emitted. A device 103 is provided for detecting gamma rays for the purpose of monitoring.

Figure 3A:
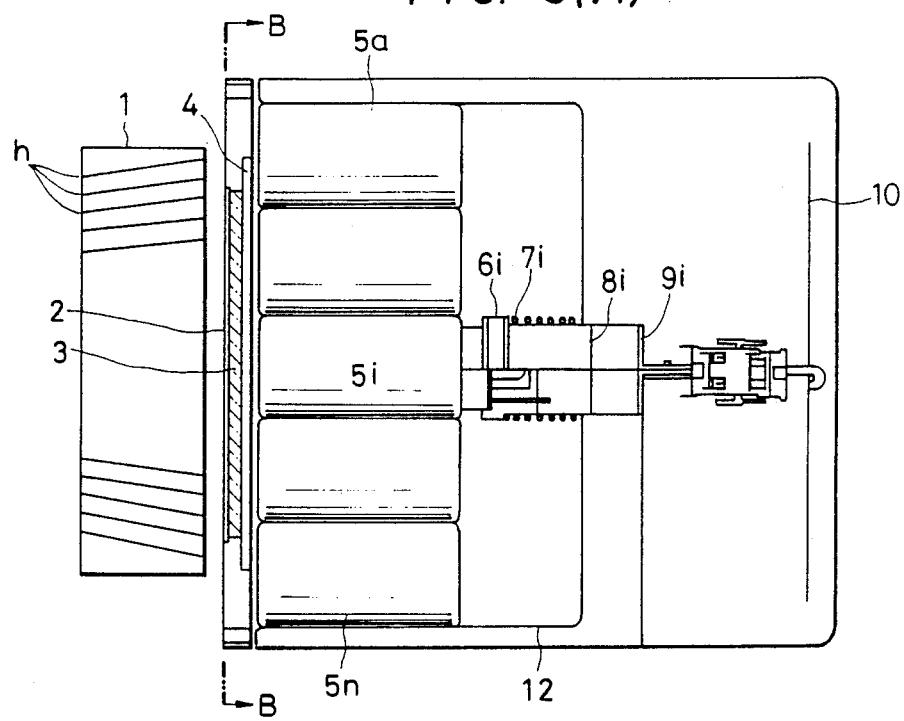
FIGS. 3(A) and 3(B) are plan and cross-sectional views, respectively, of the collimator, scintillator, and photoelectric multipliers of the apparatus of FIG. 1.

FIG. 3(A) is a plan view showing the relation among the collimator 1, the scintillator 3, and the photomultipliers 5 (5a–5n) in the casing 200. The collimator 1 has an outer diameter selected, for example, to be 210 mm so as to cover the diameter of the scintillator 3 and has fixing holes bored along a circumference of, for example, 200 mm diameter. The focal length of the collimator 1 is set, for example, to 550 mm and a number of holes h (capillaries), for example having a diameter of 1.5 mm are regularly formed in the collimator 1. The distance between the ray source 101 and the collimator 1 is selected, for example, to be 550 mm and the central axial lines of the respective capillaries are directed to the gamma ray source.

Figure 3B:
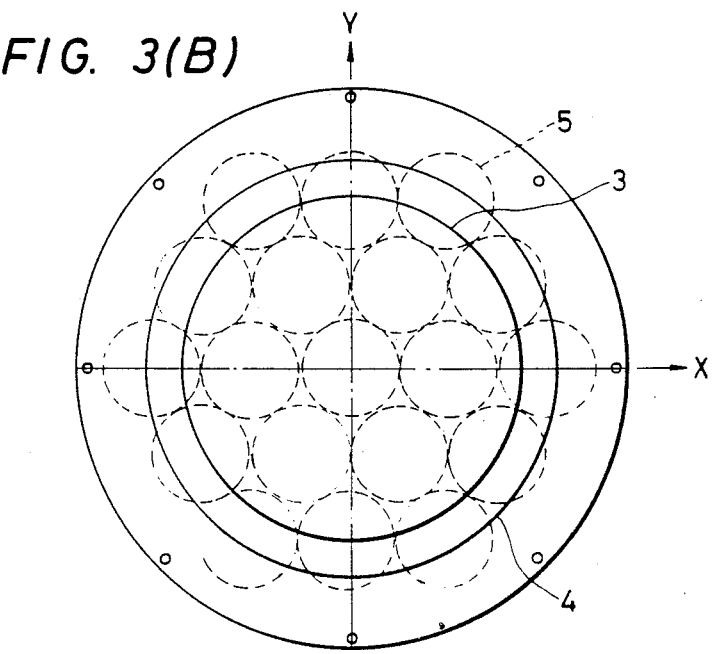

The plane scintillator 3 is sandwiched between a pair of glass plates 2 and 4 and is provided to face the emission surface of the collimator 1. The scintillator 3 is, for example, made of a crystal known by the name of NAI(TL) and converts incident gamma rays into light having a luminous emission wave length of 420 nm. photomultipliers 5a through 5n are provided to detect the luminous emissions of the scintillator 3. As shown in FIG. 3(B), the photomultiplers are arranged so that their photocathode surfaces are disposed close to each other. Each of the photomultipliers has an outer diameter of 1.5 inches (=38 mm), for example, and sockets 6a through 6n are made to correspond to the photomultipliers 5a through 5n, respectively. To facilitate understanding, only the i-th socket 6i connected to the photomultiplier 5i is shown in the drawing. The socket 6i is pressed by a spring 7i. Each socket 6i is provided with a voltage-dividing resistor substrate 8i for supplying a voltage to the electrode, such as a dynode, of the photomultiplier and a pre-amplifier substrate 9i. The reference numeral 10 designates a wiring substrate. The photomultiplers are surrounded by a magnetic shield 12.

Figure 4:
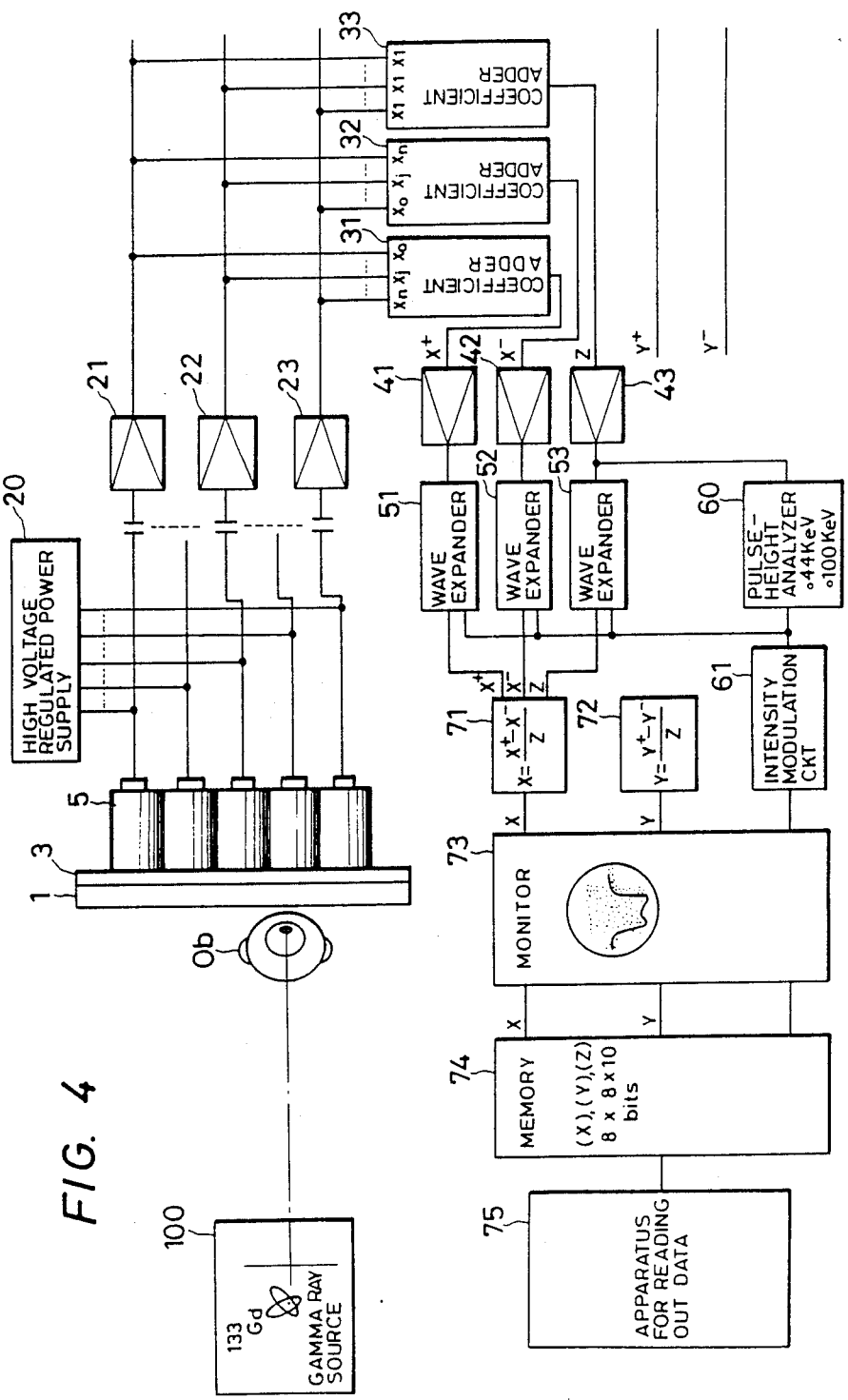
FIG. 4 is a block diagram of a circuit of the apparatus of FIG. 1.
Figure 5A:
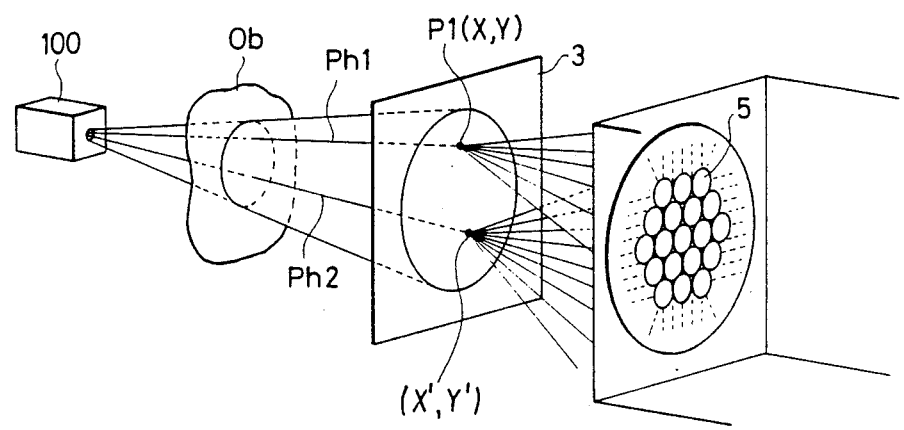
FIGS. 5(A) and 5(B) are a perspective and plan views for explaining a basic principle of this invention.
Figure 5B:
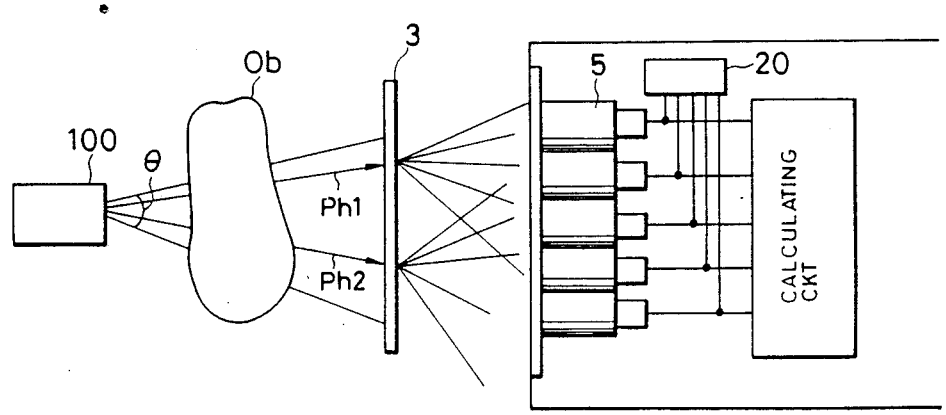

FIGS. 5(A) and 5(B) are perspective and plan views for explaining a basic principle of this invention. In the same figures, the same elements as shown in the other figures are identified by the same reference numbers. Ordinarily, there is a time interval (T) between the impact of a first gamma ray photon to a position on the surface of the scintillator 3 and the impact of a subsequent photon at another position. The impact of a gamma ray photon on the scintillator generates light having a luminous emission wave length of, for example, 420 nm. The scintillation light emitted from the scintillator is detected by each of photomultipliers 5(5a–5n), and output data (signals) from the photomultipliers are calculated by calculating circuits comprising the coefficient adders(31, 32, and 33), wave form expanders(51, 52 and 53), position operating circuits(71 and 72) and so on as shown in FIG. 4 and displayed on a monitor 73.

For example, data corresponding to an incident gamma ray photon (Ph1) to a position P1(X,Y) are calculated within a time interval that is less than the period (T) elapsing between the impact of a photon (Ph1) to the position P1(X,Y) and the impact of the next succeeding photon (Ph2) at the position P2(X', Y') as shown in FIGS. 5(A) and 5(B). In practice, as the time interval (T) is very short, elements of calculating circuits in an apparatus could not follow the variation of output data (signals) from the photomultipliers. Accordingly, it is necessary to make the variation of the output data in the circuits slower with respect to the time-axis. In order to attain the above purpose, the wave form expanders (51, 52 and 53) are provided to the calculating circuits.

FIG. 4 is a block diagram showing a circuit arrangement for use in the apparatus of the present invention. Of the photomultipliers, only the photomultiplier 5a is representatively shown. Each of the photomultipliers is supplied with an operating voltage from a high voltage regulated power supply 20. The respective outputs of the photomultipliers 5a, etc., are amplified by respective pre-amplifiers 21, 22, 23, . . . and applied to respective coefficient adders 31, 32, 33, . . .

A method of determining on the basis of output data corresponding to an incident gamma ray photon an incident position of the incident gamma ray photon (the position on the scintillator where the incident photon impinges), will be described in detail with reference to FIGS. 6(A) and 6(B).

Figure 6A:
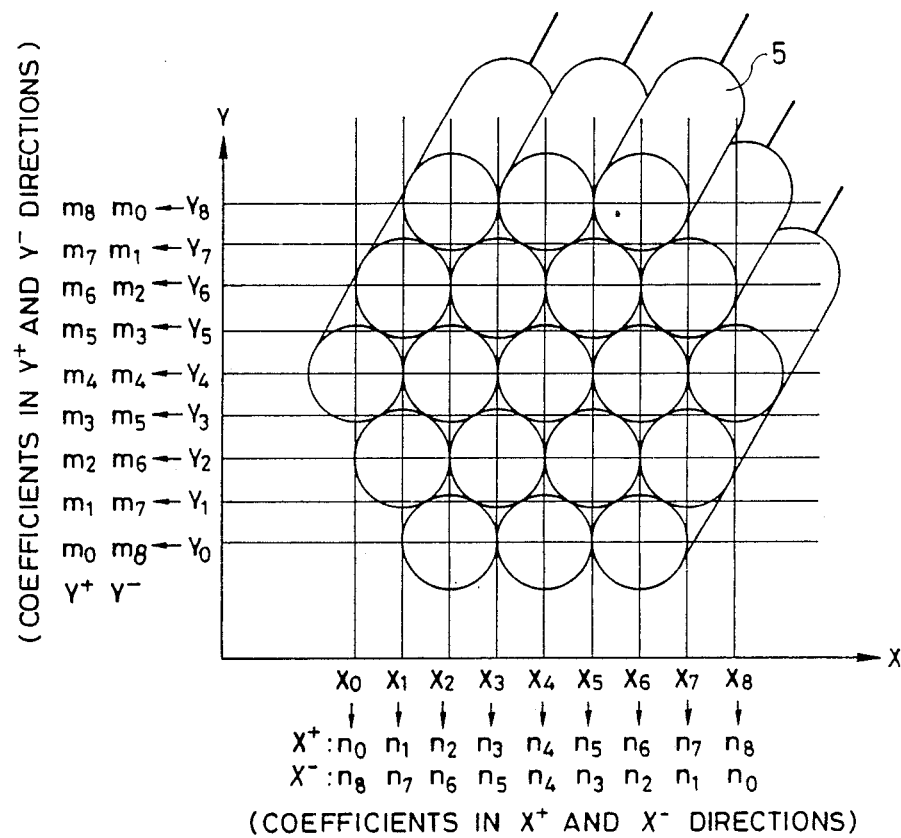
FIGS. 6(A) and 6(B) are schematic diagrams for explaining a weighting operation utilized in this invention.
Figure 6B:
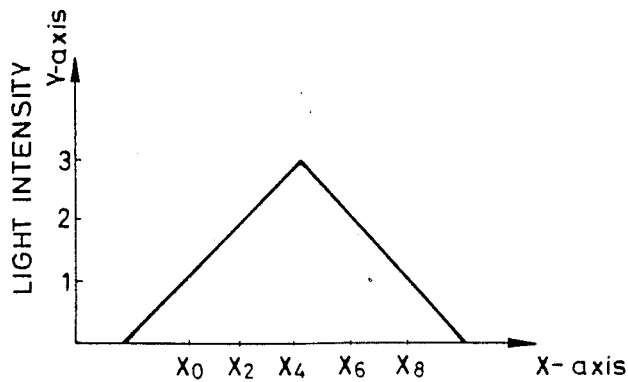

In order to facilitate understanding, for example, an arrangement of the photomultipliers as shown in FIG. 6(A) is supposed as a model arrangement of the photomultipliers. The position of the incident photon to the scintillator can be determined, for example, by subjecting the output data from the photomultipliers to a weighting operation. In the weighting operation, X-Y orthogonal coordinates are assumed with its origin determined by the arrangements of the photomultipliers. In this case, the X-Y orthogonal coordinates with the center of the above mentioned scintillator 3 as it origin is provided to the model arrangement as shown in FIG. 3(B).

In FIG. 6(A), output data of a photomultiplier at a position coordinates $(X_i, Y_i)$ in the X-Y orthogonal coordinates is represented by $a_{ij}$ ($i=0, 1, \ldots 8, j=0, \ldots 8$). In this case, a position coordinates $(X_4, Y_4)$ in the X-Y orthogonal coordinates is set to the origin (0,0), and further all values of $a_{ij}$ at the position coordinates where no photomultipliers are located are neglected or treated as zero. The respective output data $a_{ij}$ of the photomultipliers are multiplied by coefficients proportional to the position coordinates $(X_i, Y_j)$ and the resultant data are added to each other in the coefficient adders in order to obtain the four positional signals as described below.

The coefficients are divided into four groups corresponding to four directions $(X^+, X^-, Y^+$ and $Y^-)$ in the X-Y orthogonal coordinates wherein $X^+$ and $Y^+$ represent the directions of increasing values on the X-axis and Y-axis, and $X^-$ and $Y^-$ represent the negative directions of X-axis and Y-axis. The four groups of the coefficients comprise $n_i$ for $X^+$, $n_{8-i}$ for $X^-$, $m_i$ for $Y^+$ and $m_{8-i}$ for $Y^-$.

There are provided by the above calculation (multiplying and adding) the four positional signals corresponding to the four directions.

Here, the four positional signals are represented by $S(X^+)$, $S(X^-)$, $S(Y^+)$ and $S(Y^-)$, and then $$S(X^+) = \sum_{i=0}^{8}\sum_{j=0}^{8} n_i \cdot a_{ij}, \quad S(X^-) = \sum_{i=0}^{8}\sum_{j=0}^{8} n_{8-i} \cdot a_{ij},$$

$$S(Y^+) = \sum_{i=0}^{8}\sum_{j=0}^{8} m_j \cdot a_{ij}, \text{ and } S(Y^-) = \sum_{i=0}^{8}\sum_{j=0}^{8} m_{8-j} \cdot a_{ij}.$$

In this case, as the coefficients are proportional to the position coordinates, preferably, $n_i = i$ and $m_j = j$ ($i = 0, 1, \ldots 8$). The reference character Z designates the sum of the outputs $a_{ij}$ of all of the photomultipliers at a certain point in time. The respective outputs of the coefficient adders 31, 32, 33, ... are amplified by respective amplifiers 41, 42, 43, ..., and the outputs of the amplifiers are expanded by respective waveform expanders 51, 52, 53, ....

A pulse-height analyzer 60 (provided with a discriminator) monitors the level of the output Z of the amplifier 43 so as to judge whether the level is caused by the gamma ray photons of 100 kev, by the gamma ray photons of 44 kev, the gamma ray photons which impinge at the same time on the scintillator, or merely by noise. If the level is due to noise, the outputs of the waveform expanders 51, 52, 53, ... are suppressed. A signal for making the display different depending on the fact that the gamma rays are of 44 kev or of 100 kev is sent to an intensity modulation circuit 61. Thus, bone and surrounding soft tissue may be visually discriminated when displayed on a monitor 73.

The outputs of the waveform expanders 51, 52, 53, ... are subject to the operation of $(X^+ - X^-)/Z$ by a position operating circuit 71 and the operation of $(Y^+ - Y^-)/Z$ by a position operating circuit 72. For example, assuming that a scintillation light having a triangular intensity distribution in the horizontal direction as shown in FIG. 6B comes only into the photomultipliers arranged on a $Y_4$ axis (line), $$\begin{aligned}
S(X^+) &= \sum_{i=0}^{8}\sum_{j=0}^{8} n_i \, a_{ij} = \sum_{i=0}^{8}\sum_{j=0}^{8} i \cdot a_{ij} \\
&= 0 \cdot 1 + 2 \cdot 2 + 4 \cdot 3 + 6 \cdot 2 + 8 \cdot 1 \\
&= 36 \\
S(X^-) &= \sum_{i=0}^{8}\sum_{j=0}^{8} n_{8-1} \, a_{ij} = \sum_{i=0}^{8}\sum_{j=0}^{8} (8-i) \cdot a_{ij} \\
&= 8 \cdot 0 + 6 \cdot 2 + 4 \cdot 3 + 2 \cdot 2 + 0 \cdot 1 \\
&= 36 \\
S(Y^+) &= S(Y^-) = 36, \, Z = 9
\end{aligned}$$

Accordingly, $X = 0$ and $Y = 0$. It is determined on the basis of the above resultant data $(X,Y)$ that an gamma ray photon impinges on the origin of the X-Y orthogonal coordinates, that is, the center of the scintillator 3. The incident positions of gamma ray photons are determined by means of a weighting operation as described above, but this invention is not limited thereto. The results of the operations are displayed on the monitor 73 and are also stored in a memory 74. The contents of data stored in the memory 74 may be read out by a data read-out device 75 for further analysis.

The use of the apparatus will be described hereunder with respect to, by way of example, measuring the density of vertebrae of a subject.

A portion of the vertebrae to be measured is put in a space between the ray source 101 and the collimator 1. The shutter of the ray source 101 is opened. The gamma rays are transmitted through the portion of the subject to be measured and impinge on the front surface of the collimator 1. The scattered gamma rays and the other secondary radiant rays are removed by the collimator 1.

Generally, with respect to a bone, the higher the density and/or the greater the thickness, the higher the absorptivity. In such a case, it is a matter of course that the number of pulses (the number of gamma ray photons) detected in a certain period of time becomes less. In the case of a bone that is low in density and thin in thickness, the absorptivity and the number of pulses will be the opposite of the above.

The scintillator 3 emits scintillation light corresponding to the transmitted gamma ray photon every time a gamma ray photon impinges on the scintillator. The scintillator light emitted from the scintillator impinges on the surface/surfaces of one or more of the photomultipliers. The succeeding process is the same as that previously described by referring to FIG. 4, and a two-dimensional frequency distribution corresponding to a two-dimensional transmission factor distribution is stored in the memory within a predetermined period. If the thus obtained data is calibrated on the basis of the thickness of the bone of the subject, bone density can be obtained in a wide range.

The apparatus for measuring density or the like of an object having a small transmission factor according to the present invention is arranged such that gamma ray transmission in a predetermined range can be obtained at a time by using a gamma ray source for emitting gamma ray photons within a predetermined solid angle from a fixed point. A collimator is disposed with a predetermined spatial distance along an axial line from the gamma ray source corresponding to the solid angle and is provided with a number of capillaries directed to the fixed point.

The apparatus is further provided with a scintillator disposed close to the collimator, photomultipliers with their photocathodes disposed close to each other and facing the scintillator, and a position-operating integrated circuit for specifying incident positions of gamma ray photons on the scintillator on the basis of an incident unit of scintillation light impinging onto the photomultipliers and for integrating an incident frequency at every incident position. Accordingly, by using the apparatus, it is possible to collect data in the predetermined range by gamma ray radiation and positional information can be calculated immediately.

In the conventional apparatus, because a thin gamma ray beam is used, it was necessary to reduce the level of gamma rays at the ray source side collimator in order to use a thin gamma ray beam, and, therefore, efficiency of use was extremely low. In the apparatus according to the present invention, gamma rays radiated within a predetermined solid angle can be used effectively. Further, in the conventional apparatus, when data in a predetermined range was to be obtained, it was necessary to carry out scanning corresponding to the range. According to the present invention, however, data in the above-mentioned solid angle can be obtained at one time. When the apparatus according to the present invention was used for measuring bone density, determinative data could be obtained by irradiation for only two or three minutes.

It will be apparent to one of skill in the art that the present invention may be subjected to modifications and alternative arrangements without departing from the spirit and scope of applicant's general inventive concept.

What is claimed is:

1. An apparatus for measuring a physical property such as the density or the thickness of an object such as a portion of a human body, having a small transmission factor, and located at a selected measuring position, comprising:
    a gamma ray source, located at a fixed point, for emitting gamma rays comprising gamma ray photons having two distinct energy levels, constrained within a predetermined solid angle measured from the fixed point, toward the selected measuring position;
    a collimator disposed in the path of gamma rays that have been transmitted through the object, said collimator extending for a distance corresponding to the predetermined solid angle at a predetermined axial distance from said gamma ray source and including a plurality of capillaries extending therethrough, said capillaries being radially directed from said gamma ray source at the fixed point, for collimating the gamma rays transmitted through the object within said predetermined solid angle so that said collimator removes scattered gamma rays;
    a scintillator disposed closely adjacent to said collimator and having a first surface with receiving locations for receiving the gamma rays collimated by said collimator and a second surface with emitting locations for emitting light at emitting locations corresponding to the receiving locations receiving the collimated gamma rays;
    a plurality of photomultipliers disposed in an arrangement close to each other and to said second surface of said scintillator for receiving the emitted light from said emitting locations and for generating electrical signals corresponding to light intensity of the light received by said plurality of photomultipliers;
    calculating means for generating an object density spectrum for the object at the selected measuring position from said electrical signals; and
    said calculating means including means for determining for each photomultiplier generated electrical signal a corresponding one of said two distinct gamma ray photon energy levels, the result of that determination being used by said calculating means in generating the object density spectrum.

2. An apparatus according to claim 1, wherein said gamma ray source generates gamma rays with photons having energies of 44 kev and 100 kev.

3. An apparatus according to claim 1, wherein said solid angle is 16 degrees.

4. An apparatus according to claim 1, wherein said scintillator is made of crystalline material.

5. An apparatus according to claim 4, wherein said crystalline material comprises NAI (TL).

6. An apparatus according to claim 5, wherein said light emitted by said scintillator has a wave length of 420 nm.

7. An apparatus according to claim 1, wherein said calculating means includes one of a plurality of preamplifiers, each preamplifier being associated with and operatively connected to an associated one of said plurality of photomultipliers, for amplifying the electrical signals generated by said associated photomultiplier.

8. An apparatus according to claim 7, wherein said calculating means further includes a plurality of coefficient adders, each being associated with one of the plurality of preamplifiers and operatively connected thereto to receive the amplified electrical signals from its associated preamplifier, each coefficient adder generating coefficient proportional position signals representing said emitting locations of the emitted light of said associated photomultiplier in terms of X-Y coordinates determined by the arrangement of said photomultipliers.

9. An apparatus according to claim 8, wherein said calculating circuit generates said coefficient proportional position signals be a weighting operation and further includes;
    multiplier means for multiplying the amplified signals of the associated preamplifier by coefficients proportional to X-Y position coordinates of the associated photomultiplier in said X-Y coordinates; and
    adder means for adding said multiplied output signals.

10. The apparatus according to claim 8, wherein said calculating means further includes:
    a plurality of amplifiers each operatively connected to an associated one of the coefficient adders for receiving the coefficient proportional position signals from the associated coefficient adder and for generating amplified coefficient proportional position signals from the received signals;
    waveform expander means operatively connected to said plurality of amplifier means for receiving said amplified coefficient proportional position signals and for outputting waveform-expanded coefficient proportional position signals; and
    position specifying means for specifying the emitting locations of the incident gamma ray photons from the wave-expanded coefficient proportional position signals and for generating the object density spectrum by intergrating incident frequencies for each emitting location, each emitting location having an incident frequency associated therewith.

* * * * *